United States Patent [19]

Young

[11] Patent Number: 4,906,231
[45] Date of Patent: Mar. 6, 1990

[54] SINGLE-USE FILLABLE SYRINGE

[76] Inventor: J. Winslow Young, 803 E. Center St., Centerville, Utah 84014

[21] Appl. No.: 258,032

[22] Filed: Oct. 14, 1988

[51] Int. Cl.⁴ .............................................. A61M 5/00
[52] U.S. Cl. ..................................... 604/110; 604/228
[58] Field of Search ............... 604/110, 187, 218, 210, 604/209, 208, 207, 228

[56] References Cited

U.S. PATENT DOCUMENTS

| | | | |
|---|---|---|---|
| 4,252,118 | 2/1981 | Richard et al. | 604/110 |
| 4,367,738 | 1/1983 | Legendre et al. | 604/218 |
| 4,699,614 | 10/1987 | Glazier | 604/228 X |
| 4,826,483 | 5/1989 | Molnar | 604/110 |

Primary Examiner—John D. Yasko
Attorney, Agent, or Firm—J. Winslow Young

[57] ABSTRACT

A single-use disposable hypodermic syringe is described in which a plunger is initially coupled to a piston to permit filling of the syringe with fluid. During the filling step, the plunger is constrained to only move in the outward direction as required for filling. In order for injection to occur, the plunger must be rotated into a second position in which the plunger is irreversibly decoupled from the piston. In this position, the plunger is constrained so that it may only move inwardly as required for injection. The plunger and plunger guide also include corresponding sets of ribs and detents which cooperate in a rachet action to restrict the direction of travel of the plunger. This restriction means that the plunger can be pulled out only once (to draw liquid into the syringe) and pushed in only once (to expel the liquid from the syringe). Since the plunger can no longer be recoupled to the piston, and also since the plunger is locked in its forward position, re-use of the syringe is rendered impossible.

7 Claims, 2 Drawing Sheets

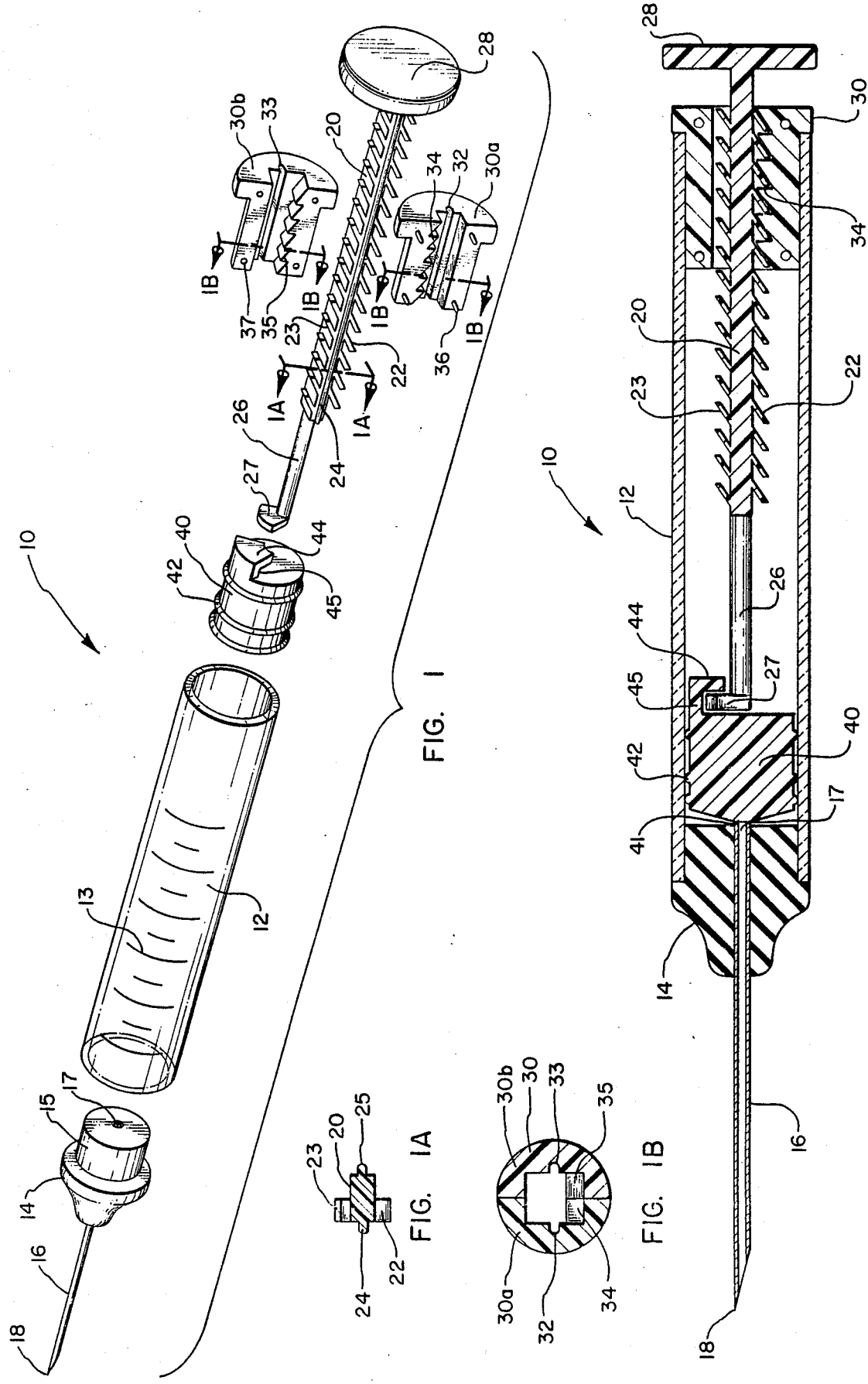

4,906,231

SINGLE-USE FILLABLE SYRINGE

BACKGROUND OF THE INVENTION

This invention relates to a disposable hypodermic syringe, which can be filled and used once, and which is designed in such a manner that re-use of the syringe is rendered impossible. The design of the present invention provides a reliable and effective way of reducing the risk of contamination when hypodermic syringes are re-used without proper sterilization. In addition, use of this hypodermic syringe would serve to curtail the spread of infectious diseases by intravenous drug users, who are known to share and re-use syringes amongst themselves.

A number of designs for non-refillable hypodermic syringes are available in the prior art. In one such design, disclosed in U.S. Pat. No. 4,650,468, the user of the syringe must twist the plunger assembly after injection is completed in order to retract the plunger and to appropriately position a piston housing assembly to engage a locking mechanism which ensures that the piston may not be moved from its retracted position. However, this type of design may not render the syringe useless after the first injection if the plunger assembly is not intentionally twisted and retracted to cause the requisite locking action. Additionally, the overall design and the number of components necessary to assemble this prior art syringe makes it overly complex and expensive to manufacture.

In another type of prior art design disclosed in U.S. Pat. No. 4,687,467, a needle extends rearwardly into the syringe and provides a sharp cutting edge which punctures the end of the piston during the final forward movement of the piston during injection. Here again, the syringe may be re-used if the piston is not pushed all the way forward to effect the puncturing. Other prior art designs also suffer from the same problem wherein someone determined to re-use the syringe may do so by circumventing the built-in safety mechanisms.

SUMMARY OF THE INVENTION

Accordingly, it is an object of the present invention to provide a design for a single use disposable syringe which ensures that re-use of the syringe is rendered impossible.

It is an additional object of this invention to provide the above-mentioned fail-proof single-use mechanism while still allowing the first user to properly fill the syringe to its prescribed capacity, and inject the contents thereof.

It is yet another object of this invention to provide the above mentioned features in a manner which minimizes the number of components required for assembly, so that the cost of assembly can be minimized.

In the present invention, the piston and plunger are separable and are designed so that the plunger is initially engaged to the piston to permit it to be pulled rearwardly for filling the syringe for the first and only time. During the filling procedure the plunger is constrained to move only rearwardly. In order to perform the injection, the plunger is rotated into a position which only permits the forward movement necessary for injection. However, upon rotation of the plunger prior to injection, the piston is irreversibly disengaged from the plunger. A subsequent refill is thereby rendered impossible.

BRIEF DESCRIPTIONS OF THE DRAWINGS

The foregoing and other objects, features, and advantages of the present invention will become more apparent from the following more detailed description of a preferred embodiment of the invention as illustrated in the accompanying drawings wherein:

FIG. 1 is an exploded isometric drawing of the syringe of this invention which shows all the component parts of the syringe. FIG. 1A and FIG. 1B are cross-sectional views of part of the plunger stem and the plunger guide respectively.

FIG. 2 is a longitudinal cross section view of the fully assembled syringe, and illustrates the position of internal components prior to filling.

DETAILED DESCRIPTION OF THE INVENTION

Figure 3:
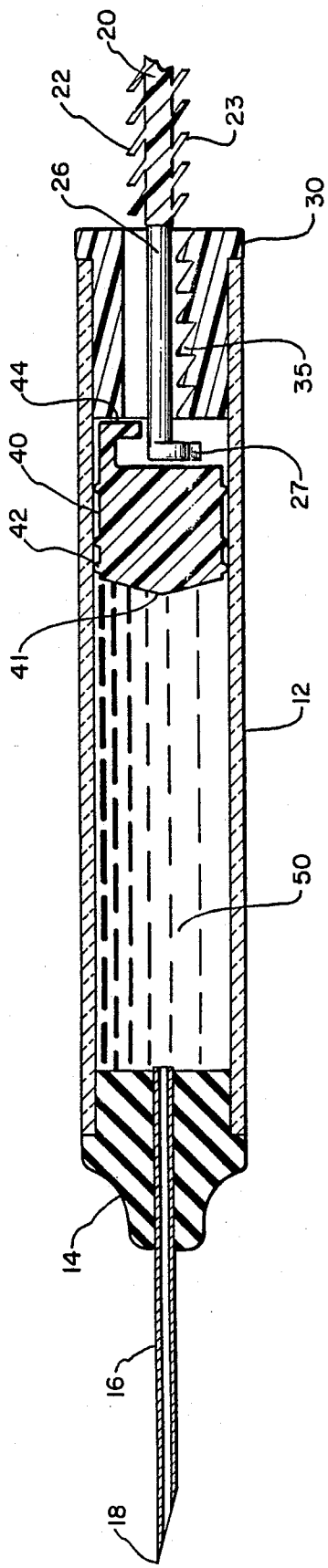
FIG. 3 is a longitudinal cross section view of the syringe after the filling step has been performed, and the plunger has been rotated into a position to permit forward motion of the piston for injection.

The novel, single-use syringe of this invention may be more particularly described by reference to FIG. 1, wherein the syringe is indicated generally by reference numeral 10 and includes a hollow, syringe barrel 12 with a needle assembly 14 mounted at one end and having a plunger 20, a plunger guide 30 (shown as constructed from two mateable sections 30a and 30b), and a piston 40 inserted in the other end. Needle assembly 14 includes a conventional hypodermic needle 16 mounted in a base 15 which is adapted to be secured in the end of syringe barrel 12 so as to expose the open end of needle base 17 to fluid 50 which can be delivered to needle point 18.

Piston 40 is generally a conventional piston for a hypodermic syringe having an apex 41 and seal ring 42. A lip 44 is formed on the edge of a partial rim 45 and serves as an engagement for foot 27 to allow piston 40 to be pulled outwardly by foot 27 when plunger 20 is pulled outwardly.

Plunger 20 is designed with a generally rectangular cross section (best seen in FIG. 1A) along most of its length except for leg 26 having a reduced cross section and terminating in foot 27. A pair of guides 24 and 25 extend outwardly as longitudinal ribs along the length of the rectangular cross sectional portion of plunger 20. A plurality of flexible ribs 22 and 23 extend outwardly at a predetermined angle from opposite faces of plunger 20. As illustrated in FIG. 2, ribs 22 point downwardly toward piston 40 while ribs 23 point upwardly toward plunger guide 30. Ribs 22 and 23 are designed to cooperate in a ratchet action with detents that form racks 34 and 35 of plunger guide 30 as will be described more fully hereinafter.

In a preferred embodiment, plunger guide 30 is fabricated in two sections, section 30a and section 30b, which can be joined together (as shown in FIG. 1B) about plunger 20 during manufacture. Each section includes a channel with guide slots 32 and 33 for guides 24 and 25 formed therein. Section 30a includes a plurality of detents formed into a rack 34 while section 30b includes another plurality of detents formed into a rack 35. Rack 34 is designed to allow ribs 22 to pass when plunger 20 is pulled out of syringe barrel 12 (to the right in FIG. 2) However, ribs 22 will immediately engage the detents of rack 34 when an attempt is made to push plunger 20 into syringe barrel 12 (to the left in FIG. 2).

This interlock/bypass cooperation between ribs 22 and rack 34 (as shown by FIG. 2) allows the user to pull plunger 20 outwardly from syringe barrel 12 while at the same time preventing reverse movement of plunger 20.

The foregoing feature restricts movement of plunger rod 20 to being pulled in one direction only until leg 26 is pulled into plunger guide 30. Leg 26 has a generally reduced cross section to allow plunger rod 20 to be rotated through 180 degrees to place ribs 23 into contact with the detents of rack 35. This is best illustrated with reference to FIG. 3. Guide 25 is now received in guide slot 32 while guide 24 is received in guide slot 33. It should also be noted that foot 27 is rotated out of engagement under lip 44. Referring particularly to FIG. 3, plunger 20 can now be pushed into syringe barrel 12 to push piston 40 toward needle assembly 14 thus expelling liquid 50 through needle throughbore 17 (FIG. 2). Any attempt to pull plunger 20 outwardly (to the right in FIG. 3) will cause ribs 23 to engage the detents of rack 35. In any event, if one were successful in pulling plunger 20 out of syringe barrel 12 after having pushed piston 40 against needle assembly 14, foot 27 no longer engages lip 44 so that piston 40 will remain in the position to which it had been pushed by foot 27.

METHOD OF MANUFACTURE AND ASSEMBLY

Needle assembly 14 may be selected from any suitable, commercially available devices and is sealed in the end of syringe barrel 12. Piston 40 may be fabricated by conventional injection molding techniques and is placed in the other end of syringe barrel 12. Foot 27 is inserted under lip 44 prior to pushing piston 40 into juxtaposition with needle assembly 14.

Plunger 20 may be fabricated by injection molding with the mold halves joining along the longitudinal axis of plunger 20. By this technique, it is possible to prepare ribs 22 and 23 in one side of the mold using relatively straightforward technology. Similar molding technology is used to create molds for sections 30a and 30b and to secure alignment of section 30a to section 30b. Prior to assembly, section 30a is fitted to one side of plunger 20 adjacent handle 28 and joined to section 30b on the other side of plunger 20. Foot 27 is then engaged under lip 44 and piston 40 pushed into syringe barrel 12 until plunger guide 30 can be secured in the end of syringe barrel 12.

Syringe 10 is now assembled, as shown in FIG. 2, and ready to be packaged and sterilized according to conventional techniques. Importantly, syringe 10 can be filled and used only once thus preventing repeated uses which is a well-known cause of transferring dangerous infections.

Although the invention herein has been described with reference to a particular embodiment, it is to be understood that this embodiment is merely illustrative of the aspects of the invention and not restrictive. Thus, it will be apparent to one skilled in the art that numerous modifications may be made to the illustrative embodiment and other arrangements may be devised which implement the invention without departing from the spirit and scope of the invention disclosed herein. Such modifications and arrangements are therefore intended to be embraced by the claims presented herein.

What I claim is:

1. A single-use hypodermic syringe having a hollow cylindrical syringe barrel, a needle assembly mounted at the forward end of the barrel, a piston slidably positioned within the barrel, a plunger, and a plunger guide affixed to the rearward end of the barrel for aligning the plunger within the barrel, the plunger having a first position in which the plunger is coupled to the piston, and a second position rotationally displaced from the first position in which the plunger is irreversibly decoupled from the piston, said plunger being rotatable between the first and second positions only when the plunger is extended towards the rear end of the barrel, means for permitting only rearward motion of the plunger when the plunger is in the first position, and means for permitting only forward motion of the plunger when the plunger is axially rotated to the second position.

2. The syringe of claim 1 wherein the plunger and the piston comprise coupling means cooperatively adapted to form an initially coupled condition when the plunger is in the first position, and to form an irreversibly decoupled condition when the plunger is rotated to the second position.

3. The syringe of claim 2 wherein the cooperatively adapted coupling means includes a lip formed on the edge of a rim affixed to the rearward face of the piston and a foot extending outwardly from the forward end of the plunger which can be engaged by the lip of the piston.

4. The syringe of claim 2 wherein the plunger guide and the plunger comprise a first means cooperatively adapted to permit only rearward motion of the plunger when the plunger is in the first position, and a second means cooperatively adapted to permit only forward motion of the plunger when the plunger is in the second position.

5. The syringe of claim 4 wherein the means for permitting only rearward motion of the plunger when the plunger is in the first position further comprises a first plurality of detents formed in the plunger guide to provide a first ratchet surface, and first plurality of flexible angled ribs formed along a side of the plunger, the first ratchet surface and the first plurality of flexible ribs cooperatively angled to permit only rearward motion of the plunger, and wherein the means for permitting only forward motion of the plunger when the plunger is in the second position comprises a second plurality of detents formed in the plunger guide to provide a second ratchet surface, and a second plurality of flexible angled ribs formed along the opposite side of the plunger, the second ratchet surface and the second plurality of flexible ribs cooperatively angled to permit only forward motion of the plunger.

6. A single-use hypodermic syringe having a hollow cylindrical syringe barrel, a needle assembly mounted at the forward end of the barrel, the syringe further comprising:
   (a) a piston slidably positioned within the barrel, said piston including means adapted to initially engage a plunger and to irreversibly disengage the plunger after a single-use of the syringe;
   (b) the plunger comprising a shank portion of substantially rectangular cross sectional area having a plurality of flexible ribs extending transversely from a front side of the shank portion to an intermediate position along the top and bottom sides of the shank position and positioned at equal intervals along the longitudinal axis of the shank portion, the ribs on the bottom side being angled forwardly towards the needle assembly, and the ribs on the top side being angled rearwardly, the shank portion further including shank portion guide means formed in the front and rear sides of the shank portion, and extending along the longitudinal axis of the shank portion, a rod having a cross section dimensioned to permit rotation within the plunger guide integrally affixed forward of the shank such that after full extension of the plunger rearwardly the plunger may be rotated, and means affixed to the forward end of the rod portion for engaging the piston during initial assembly and for irreversibly disengaging the piston when the plunger is rotated; and (c) a plunger guide affixed to the rear end of the syringe barrel, having a substantially rectangular opening adapted to receive the plunger and further comprising guide means formed in the housing to slidably couple with the shank portion guide means, a plurality of detents formed on one side of the rectangular opening in the housing to create two adjacent ratchet surfaces, a first ratchet surface having detents angled rearwardly, and extending transversely from a sidewall of the rectangular opening to the midplane of the syringe axis, and a second ratchet surface having detents angled forwardly, and extending transversely from the midplane to the opposite sidewall of the rectangular opening, so that when the forwardly angled ribs of the shank are in contact with the first ratchet surface, only rearward motion of the plunger is possible, and when the rearwardly angled ribs are in contact with the second ratchet surface, only forward motion of the plunger is possible.

7. The plunger guide of claim 6 which further comprises two sections which can be mated around the plunger for ease in assembly, wherein the first ratchet surface is formed in one section, and the second ratchet surface is formed in the second section.

* * * * *